United States Patent [19]

Eidenbenz et al.

[11] Patent Number: 5,342,696
[45] Date of Patent: Aug. 30, 1994

[54] BLANK FOR THE PRODUCTION OF A DENTAL MOULD PART

[75] Inventors: Stefan Eidenbenz, Winkel; Claude Nowak, Wettingen, both of Switzerland

[73] Assignee: Mikrona Technologie A.G., Spreitenbach, Switzerland

[21] Appl. No.: 774,097

[22] Filed: Nov. 8, 1991

[30] Foreign Application Priority Data

Oct. 10, 1990 [CH] Switzerland ............... 3264/90

[51] Int. Cl.$^5$ ............................... A61C 13/083
[52] U.S. Cl. ................... 428/542.8; 269/287; 433/49
[58] Field of Search ............... 433/49, 229; 428/542.8; 269/287

[56] References Cited

U.S. PATENT DOCUMENTS

| | | | |
|---|---|---|---|
| 3,004,343 | 10/1961 | Rydin | 433/203.1 |
| 4,575,805 | 3/1986 | Moermann et al. | 433/55 X |
| 4,615,678 | 10/1986 | Moemann et al. | 433/201.1 |
| 4,644,768 | 2/1987 | Nowak et al. | 70/492 |
| 4,890,716 | 1/1990 | Kitamura | 198/803.01 |
| 4,991,706 | 2/1991 | Kitamura | 198/346.1 |
| 5,089,312 | 2/1992 | Kawase et al. | 428/138 X |

FOREIGN PATENT DOCUMENTS 0160797 11/1985 European Pat. Off. .
0219107 4/1987 European Pat. Off. .

*Primary Examiner*—Henry F. Epstein
*Attorney, Agent, or Firm*—Egli International

[57] ABSTRACT

A ceramic blank body (2) of a blank (1) is glued on the base (4) of a support (3) of aluminum, which support bears an anchoring part on the side facing away from the blank body (2). According to the invention, the anchoring part is designed as a conical pin (6) which is rotationally symmetrical about a support axis (5). It has a circular engagement groove (7). The base (4) is provided with a bore (8) parallel to the support axis (5). For working the blank, the pin (6) is introduced into a receiving opening (10) of a holding device (9) as far as the limit stop, which is produced by the conical circumferential surface of the pin (6) coming into contact with the analogously conical periphery of the receiving opening (10), and is secured by means of a ball (11) projecting into the engagement groove (7) under the action of an elastic ring (12). A securing pin (13) projects into the bore (8) of the base (4) in order to secure the blank (1) against turning. An ejector (14) arranged at the bottom of the receiving opening is used for removing the blank (1). The blank (1) is secured on a clamp (15), which is pressed by means of a nut (17) against a clamp support (16).

8 Claims, 2 Drawing Sheets

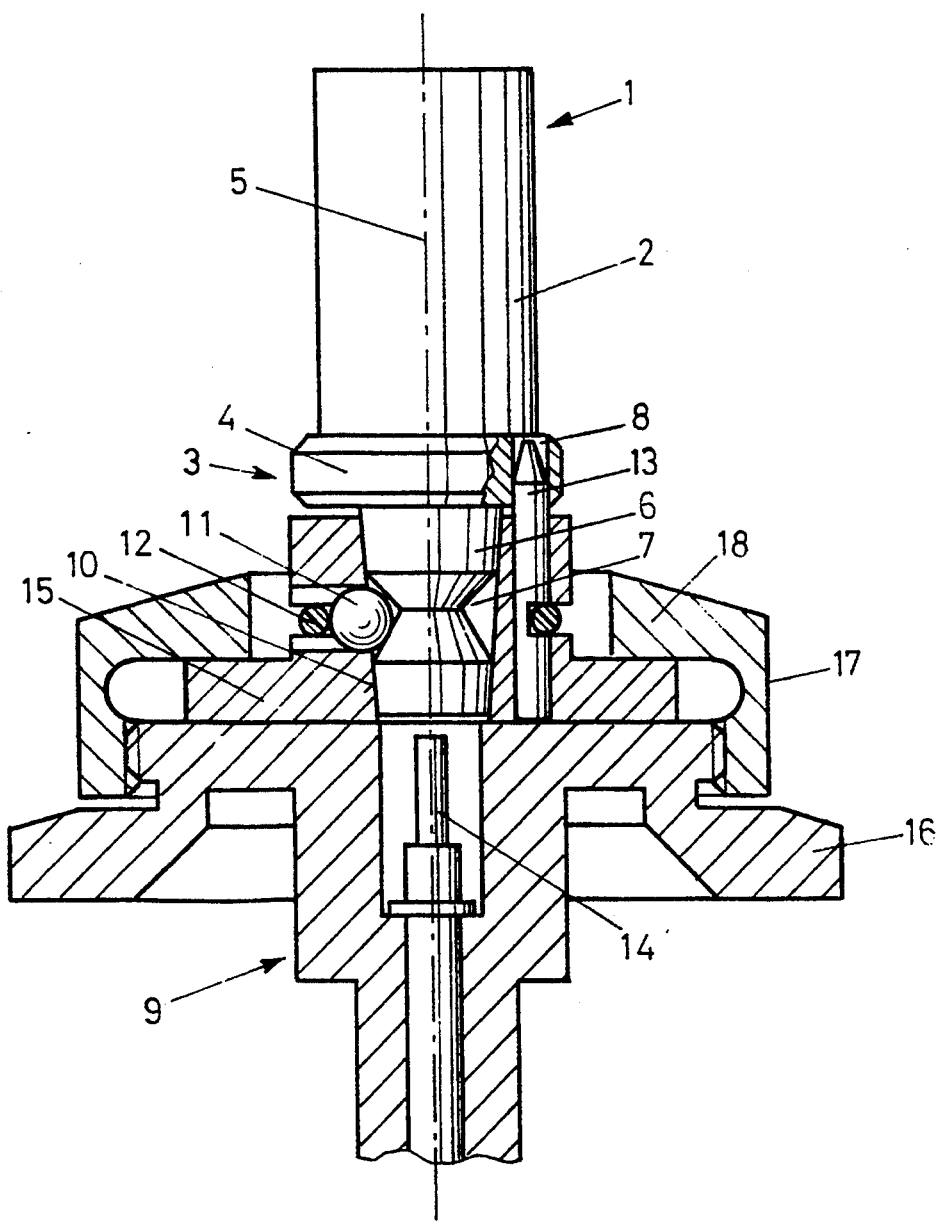

BLANK FOR THE PRODUCTION OF A DENTAL MOULD PART

BACKGROUND OF THE INVENTION

1. Field of Invention

The invention relates to a blank for the production of a dental mould part and a holding device for the same.

Blanks of the type mentioned are used for producing inlays, onlays, crowns etc. in dentistry. The part in question is worked from the blank by milling or similar working techniques using a model taken from the prepared tooth or else, with numerical control, using a measurement of the tooth effected by optical or other means.

For this purpose, on account of the low work tolerances, a very precise and secure clamping of the blank in a holding device is necessary. In the event of reclamping following removal from the holding device for the purpose of checking or subsequent machining, it must be possible for the original position to be reproduced exactly.

2. Description of Related Art

A blank of the generic type is known (EP-A-0 160 797) in which a blank body is secured on a support which bears on the side facing away from the blank body an anchoring part of essentially circular cylindrical shape. However, it is only with difficulty that such an anchoring part can be clamped in a holding device rigidly and at the same time completely free of play, since, for instance, a similarly cylindrical receiving opening, which should permit the straightforward insertion of the anchoring part as far as a limit stop necessary for definition of the position in the axial direction and a likewise straightforward removal, must by necessity have a slightly greater diameter than the anchoring part. A resilient design of the parts of the holding device coming into contact with the blank, which design would in principle permit clamping free of play, can hardly be considered on account of the high precision requirements.

SUMMARY OF THE INVENTION

It is the object of this invention to provide a blank for the production of dental mould parts, which blank can be clamped completely free of play in a simple holding device, and the invention additionally provides a corresponding holding device. An insertion of the anchoring part as far as the limit stop defines the position of the blank in the direction of insertion and at the same time fixes its position with respect to the remaining degrees of freedom exactly and completely free of play.

The advantages afforded by the invention lie principally in the fact that the position of the blank can be set extremely precisely and in a reproducible manner with low outlay, above all also in the design of the holding device. In addition, the holding device can easily be designed such that insertion and removal of the blank is possible in an extremely simple way, without closing and opening of any locking mechanisms. The blank and holding device are suitable very particularly for the production of dental mould parts by copy-milling from models.

BRIEF DESCRIPTION OF THE DRAWINGS

The invention is discussed in greater detail hereinbelow with reference to figures which illustrate only one exemplary embodiment and in which:

FIG. 1 shows, in a vertical section, a blank according to the invention in a holding device according to the invention, illustrated in a cutaway view.

DETAILED DESCRIPTION OF THE DRAWINGS

The blanks 1 illustrated in the figures in each case have a blank body 2, preferably of ceramic material, and a support 3 which is preferably made in one piece from metal, in particular aluminum. The support 3 consists of an anchoring part and a base 4 on which the blank body 2 is secured, preferably by gluing.

Figure 2A:
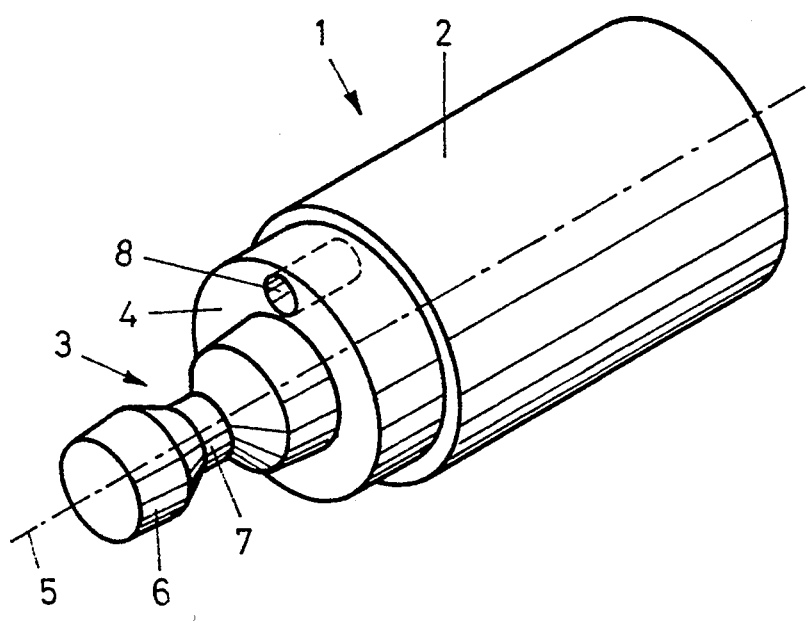
FIGS. 2a, 2b show, in a perspective illustration, two embodiments of a blank according to the invention.
Figure 2B:
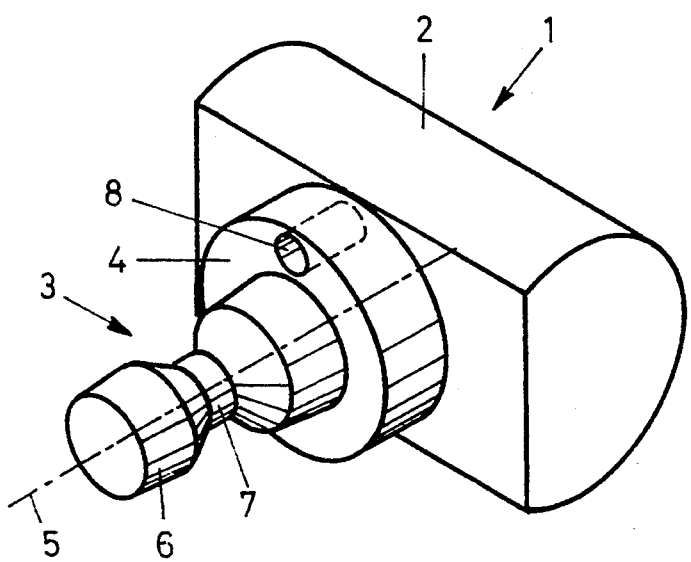

According to the invention, the anchoring part is designed as a conical pin 6 which widens towards the base 4 and which is essentially rotationally symmetrical about a support axis 5 intersecting the blank body 2. It has a circular engagement groove 7 for the engagement of a retention device. The engagement groove can be designed, for example, as shown in FIG. 1 or as shown in FIGS. 2a, 2b.

The base 4 is designed as a small circular plate coaxial to the pin. It comprises eccentrically a bore 8 which is parallel to the support axis 5 and is intended for the engagement of a securing part effective against turning of the blank 1.

The blank body 2 is in general of approximately cylindrical design (other shapes, such as cuboids, are of course also possible), the height being greater than the diameter. Depending on the shape and position of the mould part to be milled, it may be advantageous to secure the blank body 2 on the support 3 in such a way that its axis coincides approximately with the support axis 5 (FIG. 2a) or approximately forms a right angle to it (FIG. 2b).

The holding device 9, into which the blank 1 is clamped for machining, has a receiving opening 10 which is rotationally symmetrical about an opening axis, which coincides with the support axis 5, and narrows conically inwards exactly analogous to the outer surface of the pin 6. A ball 11 is mounted in a bore opening laterally into the receiving opening 10, this ball engaging as a retention device into the engagement groove 7 and, by means of the pressure it exerts on the lower conical edge surface, holds the pin 6 securely in the receiving opening 10. During insertion and removal of the pin 6, the ball is pushed back counter to the spring force of a ring 12 of elastic material, which surrounds the receiving opening 10 and acts on the outside of the ball 11 facing away from the opening. For insertion of the pin 6, the latter need only be pressed into the receiving opening 10. The lower part of its conical circumferential surface then forces the ball 11 back into the lateral bore. When the pin 6 reaches its limit stop, i.e. when the said conical circumferential surface sits snugly on the conical periphery of the receiving opening 10, the ball 11 assumes the position illustrated in FIG. 1 under the action of the ring 12. It projects into the engagement groove 7 and holds the pin 6 securely, while pressing against the upwardly inclined lower edge surface of the engagement groove 7. For removal, the blank 1 need only be pulled upwards with sufficient force so that the said lower edge surface of the engagement groove 7 presses the ball 11 outwards. There is no need for any locking mechanisms to be closed and opened.

In order to secure the blank 1 against turning, a securing pin 13 is arranged alongside the receiving opening, this pin tapering upwards and engaging in the bore 8 in the base 4 of the support 3. The securing pin 13 is dimensioned in such a way that the lower part of its section projecting into the bore 8 has a slightly greater diameter than the bore, at least transverse to the connection line between securing pin 13 and opening axis, so that the base 4 in the area of the bore 8 is slightly deformed upon clamping of the blank 1. In this way, play in the azimuthal direction is completely avoided and, in the event of removal and reclamping, the position of the blank 1 can be exactly reproduced in this respect too. The securing pin 13 must of course consist of a harder material than the support 3, preferably steel.

Arranged at the bottom of the receiving opening 10 is an ejector 14 which can be displaced in the direction of the opening axis from the outside using an activating rod, and which is used for removing the blank 1 from the holding device 9.

The receiving opening 10 and the securing pin 13 are arranged on a clamp 15 which bears on a plane surface of a clamp support 16, perpendicular to the opening axis, and is displaceable along this surface after detachment of a fastening arrangement. The fastening arrangement is formed by a nut 17 which is screwed to the clamp support 16 and which, by means of an inwardly projecting holding flange 18, engages over a flange surrounding the clamp 15 and presses it against the clamp support 16.

We claim:

1. A blank (1) for the production of a dental mould part, comprising a blank body (2) of dental restoration material and a support (3) to which the blank body (2) is securely connected, the support having, on a side facing away from the blank body, an anchoring part so that the blank (1) is anchorable to a holding device (9) having a receiving opening, the anchoring part having at least one conical section which is essentially rotationally symmetrical about a support axis (5) intersecting the blank body (2) and which widens in a direction of the body, for making contact with at least part of a receiving opening (10) of the holding device (9).

2. The blank (1) of claim 1, wherein the anchoring part has at least one working surface engagable with a retention device, which surface is inclined relative to the blank body (2).

3. The blank (1) of claim 2, wherein the anchoring part is an essentially conical pin (6) which is rotationally symmetrical about the support axis (5), and the working surface is a conical edge surface of an engagement groove (7).

4. The blank (1) of claim 1, wherein the support (3) has a base (4) which extends essentially transverse to the support axis and on which the blank body (2) is secured, and which has a recess in which a securing part is engageable to prevent turning of the blank (1).

5. The blank (1) of claim 4, wherein the recess is a bore (8) approximately parallel to the support axis (5).

6. The blank (1) of claim 1, wherein the blank body (2) has a main direction of extension that coincides with the direction of the support axis (5).

7. The blank (1) of claim 1, wherein the blank body (2) has a main direction of extension that forms a right angle with the support axis (5).

8. A blank for production of a dental mould part, comprising a blank body of dental restoration material, and a support to which the blank body is fixed, the support having, on a side facing away from the blank body, an anchoring portion, the anchoring portion having at least one conical section that is essentially rotationally symmetrical about a support axis that intersects the blank body, the conical section widening in a direction of the blank body, the support having a base that is essentially transverse to the support axis and on which the blank body is fixed, the base having a bore therein approximately parallel to the support axis so as to permit engagement of a securing member to prevent turning of the blank.

* * * * *